United States Patent [19]
Glover et al.

[11] Patent Number: 5,879,623
[45] Date of Patent: Mar. 9, 1999

[54] METHODS AND COMPOSITIONS FOR CONTROLLING BIOFOULING USING FLUOROSURFACTANTS

[75] Inventors: Daniel E. Glover, Brighton, Tenn.; Joe C. Steelhammer, West Point, Miss.; Stephen D. Bryant, Bartlett, Tenn.

[73] Assignee: Buckman Laboratories International Inc., Memphis, Tenn.

[21] Appl. No.: 579,365

[22] Filed: Dec. 27, 1995

[51] Int. Cl.$^6$ .............................. C23F 11/00; B01J 13/00; B01D 17/04
[52] U.S. Cl. ........................... 422/14; 252/325; 252/331; 427/2.1; 427/2.29; 427/230
[58] Field of Search ............................. 422/14; 252/325, 252/331, DIG. 1; 427/2.1, 2.29, 230

[56] References Cited

U.S. PATENT DOCUMENTS

| | | | |
|---|---|---|---|
| 4,089,804 | 5/1978 | Falk | 252/355 |
| 4,144,185 | 3/1979 | Block | 252/180 |
| 4,470,964 | 9/1984 | Chang | 424/52 |
| 4,759,925 | 7/1988 | Gaffar et al. | 424/52 |
| 4,975,109 | 12/1990 | Friedman, Jr. et al. | 71/67 |
| 4,992,260 | 2/1991 | Caslavsky et al. | 424/52 |
| 5,100,649 | 3/1992 | Caslavsky et al. | 424/52 |
| 5,256,182 | 10/1993 | Friedman, Jr. et al. | 504/124 |

FOREIGN PATENT DOCUMENTS

| | | |
|---|---|---|
| 0 310 753 | 4/1989 | European Pat. Off. . |
| 0 742 282 | 11/1996 | European Pat. Off. . |
| 43 33 385 | 4/1995 | Germany . |
| WO 95/20642 | 8/1995 | WIPO . |

OTHER PUBLICATIONS

C. Kent, "Biological Fouling: Basic Science and Models", pp. 207–221 (in Malo, L. F., Bott, T.R., Bernardo, C.A., (eds.), Fouling Science and Technology, NATO ASI Series, Series E, Applies Sciences: No. 145, Kluever Acad. Publishers, Dordrecht, The Netherlands, 1988).

*Primary Examiner*—Nina Bhat
*Attorney, Agent, or Firm*—Morgan, Lewis & Bockius LLP

[57] ABSTRACT

The present invention relates to a method to inhibit bacteria from adhering to a submergible surface. The method contacts the submergible surface with an effective amount of at least one fluorosurfactant to inhibit bacterial adhesion to the submergible surface. The present invention also relates to a method for controlling biofouling of an aqueous system. This method adds an effective amount of at least one fluorosurfactant to inhibit bacteria from adhering to a submerged surface within the aqueous system. This method effectively controls biofouling without substantially killing the bacteria fouling organisms. The fluorosurfactant used in the method of the invention is an anionic or nonionic fluorosurfactant selected from: $R_fCH_2CH_2SCH_2CH_2CO_2Li$, $(R_fCH_2CH_2O)P(O)(ONH_4)_2$, $(R_fCH_2CH_2O)_2P(O)(ONH_4)$, $(R_fCH_2CH_2O)P(O)(OH)_2$, $(R_fCH_2CH_2O)_2P(O)(OH)$, $R_fCH_2CH_2O(CH_2CH_2O)_xH$, $R_fCH_2CH_2O(CH_2CH_2O)_yH$, $R_fCH_2CH_2SO_3H$, or mixtures thereof. The group $R_f$ is $F(CF_2CF_2)_{3-8}$, x varies from 2-20, and y varies from 2-20. The present invention also relates to a compositions containing a fluorosurfactant and useable in the above methods. The compositions comprise at least one fluorosurfactant in an amount effective to inhibit bacteria from adhering to submergible or submerged surfaces.

26 Claims, No Drawings

METHODS AND COMPOSITIONS FOR CONTROLLING BIOFOULING USING FLUOROSURFACTANTS

BACKGROUND OF THE INVENTION

1. Field of the Invention

The invention uses fluorosurfactants to inhibit bacterial adhesion to submergible or submerged surfaces, particularly those surfaces within an aqueous system. The invention also relates to methods and compositions for controlling biological fouling.

2. Description of Related Art

Microorganisms adhere to a wide variety of surfaces, particularly surfaces in contact with aqueous fluids which provide a suitable environment for microbial growth. For example, microorganisms are known to adhere to ship hulls, marine structures, teeth, medical implants, cooling towers, and heat exchangers. Adhering to such submerged or submergible surfaces, microorganisms may foul the surface or cause it to deteriorate.

In mammals, (e.g., humans, livestock, pets), microorganisms adhered to a surface may lead to health problems. Plaque, for example, results from microorganisms adhering to the surfaces of teeth. Medical implants with unwanted microorganism adhered to their surfaces often become crusted over and must be replaced.

Scientific studies have shown that the first stage of biofouling in aqueous systems is generally the formation of a thin biofilm on submerged or submergible surfaces, i.e., surfaces exposed to the aqueous system. Attaching to and colonizing on a submerged surface, microorganisms such as bacteria, are generally thought to form the biofilm and modify the surface to favor the development of the more complex community of organisms that make up the advanced biofouling of the aqueous system and its submerged surfaces. A general review of the mechanisms and importance of biofilm as the initial stage in biofouling is given by C. A. Kent in "Biological Fouling: Basic Science and Models" (in Melo, L. F., Bott, T. R., Bernardo, C. A. (eds.), Fouling Science and Technology, NATO ASI Series, Series E, Applied Sciences: No. 145, Kluwer Acad. Publishers, Dordrecht, The Netherlands, 1988). Other literature references include M. Fletcher and G. I. Loeb, Appl. Environ. Microbiol. 37 (1979) 67–72; M. Humphries et. al., FEMS Microbiology Ecology 38 (1986) 299–308; and M. Humphries et. al., FEMS Microbiology Letters 42 (1987) 91–101.

Biofouling, or biological fouling, is a persistent nuisance or problem in a wide varieties of aqueous systems. Biofouling, both microbiological and macro biological fouling, is caused by the buildup of microorganisms, macro organisms, extracellular substances, and dirt and debris that become trapped in the biomass. The organisms involved include microorganisms such as bacteria, fungi, yeasts, algae, diatoms, protozoa, and macro organisms such as macro algae, barnacles, and small mollusks like Asiatic clams or Zebra Mussels.

Another objectionable biofouling phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and have a characteristic, undesirable odor that is different from that of the aqueous system in which it formed. The microorganisms involved in slime formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms.

Biofouling, which often degrades an aqueous system, may manifest itself as a variety of problems, such as loss of viscosity, gas formation, objectionable odors, decreased pH, color change, and gelling. Additionally, degradation of an aqueous system can cause fouling of the related water-handling system, which may include, for example, cooling towers, pumps, heat exchangers, and pipelines, heating systems, scrubbing systems, and other similar systems.

Biofouling can have a direct adverse economic impact when it occurs in industrial process waters, for example in cooling waters, metal working fluids, or other recirculating water systems such as those used in papermaking or textile manufacture. If not controlled, biological fouling of industrial process waters can interfere with process operations, lower process efficiency, wasting energy, plug the water-handling system, and even degrade product quality.

For example, cooling water systems used in power plants, refineries, chemical plants, air-conditioning systems, and other industrial operations frequently encounter biofouling problems. Airborne organisms entrained from cooling towers as well as waterborne organisms from the system's water supply commonly contaminate these aqueous systems. The water in such systems generally provides an excellent growth medium for these organisms. Aerobic and heliotropic organisms flourish in the towers. Other organisms grow in and colonize such areas as the tower sump, pipelines, heat exchangers, etc. If not controlled, the resulting biofouling can plug the towers, block pipelines, and coat heat-transfer surfaces with layers of slime and other biologic mats. This prevents proper operation, reduces cooling efficiency and, perhaps more importantly, increases the costs of the overall process.

Industrial processes subject to biofouling also include papermaking, the manufacture of pulp, paper, paperboard, etc. and textile manufacture, particularly water-laid non-woven textiles. These industrial processes generally recirculate large amounts of water under conditions which favor the growth of biofouling organisms.

Paper machines, for example, handle very large volumes of water in recirculating systems called "white water systems." The furnish to a paper machine typically contains only about 0.5% of fibrous and non-fibrous papermaking solids, which means that for each ton of paper almost 200 tons of water pass through the headbox. Most of this water recirculates in the white water system. White water systems provide excellent growth media for biofouling microorganisms. That growth can result in the formation of slime and other deposits in headboxes, waterlines, and papermaking equipment. Such biofouling not only can interfere with water and stock flows, but when loose, can cause spots, holes, and bad odors in the paper as well as web breaks—costly disruptions in paper machine operations.

Biofouling of recreational waters such as pools or spas or decorative waters such as ponds or fountains can severely detract from people's enjoyment of them. Biological fouling often results in objectional odors. More importantly, particularly in recreational waters, biofouling can degrade the water quality to such an extent that it becomes unfit for use and may even pose a health risk.

Sanitation waters, like industrial process waters and recreational waters, are also vulnerable to biofouling and its associated problems. Sanitation waters include toilet water, cistern water, septic water, and sewage treatment waters. Due to the nature of the waste contained in sanitation waters, these water systems are particularly susceptible to biofouling.

To control biofouling, the art has traditionally treated an affected water system with chemicals (biocides) in concentrations sufficient to kill or greatly inhibit the growth of biofouling organisms. See, e.g., U.S. Pat. Nos. 4,293,559 and 4,295,932. For example, chlorine gas and hypochlorite solutions made with the gas have long been added to water systems to kill or inhibit the growth of bacteria, fungi, algae, and other troublesome organisms. However, chlorine compounds may not only damage materials used for the construction of aqueous systems, they may also react with organic materials to form undesirable substances in effluent streams, such as carcinogenic chloromethanes and chlorinated dioxins. Certain organic compounds, such as methylenebisthiocyanates, dithiocarbamates, haloorganics, and quaternary ammonium surfactants, have also been used. While many of these are quite efficient in killing microorganisms or inhibiting their growth, they may also be toxic or harmful to humans, animals, or other non-target organisms.

One possible way to control the biofouling of aqueous systems, which include the associated submerged surfaces, would be to prevent or inhibit bacterial adhesion to submerged surfaces within the aqueous system. This can be done, of course, using microbicides which, however, generally suffer from some of the disadvantages mentioned above. As an alternative, the present invention provides methods and compositions useful to substantially inhibit bacterial adhesion to a submerged or submergible surface and to control biofouling of aqueous systems. The invention obviates the disadvantages of prior methods. Other advantages of this invention will become apparent from a reading of the specifications and appended claims.

SUMMARY OF THE INVENTION

The present invention relates to a method to inhibit bacteria from adhering to a submergible surface. The method contacts the submergible surface with an effective amount of at least one fluorosurfactant to inhibit bacteria from adhering to the submergible surface. The fluorosurfactant used in the method is an anionic or nonionic selected from: $R_fCH_2CH_2SCH_2CH_2CO_2Li$, $(R_fCH_2CH_2O)P(O)(ONH_4)_2$, $(R_fCH_2CH_2O)_2P(O)(ONH_4)$, $(R_fCH_2CH_2O)P(O)(OH)_2$, $(R_fCH_2CH_2O)_2P(O)(OH)$, $R_fCH_2CH_2O(CH_2CH_2O)_xH$, $R_fCH_2CH_2O(CH_2CH_2O)_yH$, $R_fCH_2CH_2SO_3H$, or mixtures thereof, wherein $R_f$ is $F(CF_2CF_2)_{3-8}$, x and y each vary independently from 2–20.

The present invention relates also to a method for controlling biofouling of an aqueous system. This method adds to an aqueous system an effective amount of at least one fluorosurfactant described above to inhibit bacteria from adhering to submerged surfaces within the aqueous system. This method effectively controls biofouling without substantially killing the bacteria.

The present invention also relates to a composition for controlling biofouling of an aqueous system. The compositions comprises at least one fluorosurfactant described above in an amount effective to inhibit bacteria from adhering to submerged surfaces within the aqueous system.

DETAILED DESCRIPTION OF THE INVENTION

In one embodiment, this invention relates to a method to inhibit bacteria from adhering to a submergible surface. A submergible surface is one which may at least partially be covered, overflowed, or wetted with a liquid such as water or another aqueous fluid or liquid. The surface may be intermittently or continually in contact with the liquid. As discussed above, examples of submergible surfaces include, but are not limited to ship or boat hulls, marine structures, teeth, medical implants, surfaces within an aqueous system such as the inside of a pump, pipe, cooling tower, or heat exchanger. A submergible surface may be composed of hydrophobic, hydrophilic, or metallic materials. Advantageously, using an anionic or nonionic fluorosurfactant according to invention can effectively inhibit bacteria from adhering to hydrophobic, hydrophilic, or metallic submergible or submerged surfaces.

To inhibit the adhesion of a bacteria to a submergible surface, the method contacts the submergible surface with a fluorosurfactant. The surface is contacted with an effective amount of a fluorosurfactant, or mixture of fluorosurfactants, to inhibit bacterial adhesion to the surface. The fluorosurfactant may be applied to the submergible surface using means known in the art. For example as discussed below, the fluorosurfactant may be applied by spraying, coating or dipping the surface with a liquid formulation containing the fluorosurfactant. Alternatively, the fluorosurfactant may be formulated in a paste which is then spread or brushed on the submergible surface. Advantageously, the fluorosurfactant may be a component of a composition or formulation commonly used with a particular submergible surface.

"Inhibiting bacteria from adhering" to a submergible surface means to allow a scant or insignificant amount of bacterial adhesion for a desired period of time. Preferably, essentially no bacterial adhesion occurs and more preferably, it is prevented.

The amount of fluorosurfactant employed should allow only scant or insignificant bacterial adhesion and may be determined by routine testing. Preferably, the amount of fluorosurfactant used is sufficient to apply at least a monomolecular film of fluorosurfactant to the submergible surface. Such a film preferably covers the entire submergible surface.

Contacting a submergible surface with a fluorosurfactant according to this method allows the surface to be pretreated against bacterial adhesion. Accordingly, the surface may be contacted with a fluorosurfactant then submerged in the aqueous system.

The present invention relates also to a method for controlling biofouling of an aqueous system. An aqueous system comprises not only the aqueous fluid or liquid flowing through the system but also the submerged surfaces associated with the system. Submerged surfaces are those surfaces in contact with the aqueous fluid or liquid. Like the submergible surfaces discussed above, submerged surfaces include, but are not limited to, the inside surfaces of pipes or pumps, the walls of a cooling tower or headbox, heat exchangers, screens, etc. In short, surfaces in contact with the aqueous fluid or liquid are submerged surfaces and are considered part of the aqueous system.

The method of the invention adds at least one fluorosurfactant to the aqueous system in an amount which effectively inhibits bacteria from adhering to a submerged surface within the aqueous system. At the concentration used, this method effectively controls biofouling of the aqueous system without substantially killing the bacteria.

"Controlling biofouling" of the aqueous system means to control the amount or extent of biofouling at or below a desired level and for a desired period of time for the particular system. This can eliminate biofouling from the aqueous system, reduce the biofouling to a desired level, or prevent biofouling entirely or above a desired level.

According to the present invention, "inhibiting bacteria from adhering" to a submerged surface within the aqueous system means to allow a scant or insignificant amount of bacterial adhesion for a desired period of time for the particular system. Preferably, essentially no bacterial adhesion occurs and more preferably, bacterial adhesion is prevented. Using a fluorosurfactant according to the invention can, in many cases, break up or reduce other existing attached microorganisms to undetectable limits and maintain that level for a significant period of time.

While some fluorosurfactants may exhibit biocidal activity at concentrations above certain threshold levels, fluorosurfactants effectively inhibit bacterial adhesion at concentrations generally well below such threshold levels. According to the invention, the fluorosurfactant inhibits bacterial adhesion without substantially killing the bacteria. Thus, the effective amount of a fluorosurfactant used according to the invention is well below its toxic threshold, if the fluorosurfactant also has biocidal properties. For example, the concentration of the fluorosurfactant may be ten or more times below its toxic threshold. Preferably, the fluorosurfactant should also not harm non-target organisms which may be present in the aqueous system.

A fluorosurfactant, or a mixture of fluorosurfactants, may be used to control biofouling in a wide variety of aqueous systems such as those discussed above. These aqueous systems include, but are not limited to, industrial aqueous systems, sanitation aqueous systems, and recreational aqueous systems. As discussed above, examples of industrial aqueous systems are metal working fluids, cooling waters (e.g., intake cooling water, effluent cooling water, and recirculating cooling water), and other recirculating water systems such as those used in papermaking or textile manufacture. Sanitation aqueous systems include waste water systems (e.g., industrial, private, and municipal waste water systems), toilets, and water treatment systems, (e.g., sewage treatment systems). Swimming pools, fountains, decorative or ornamental pools, ponds or streams, etc., provide examples of recreational water systems.

The effective amount of a fluorosurfactant to inhibit bacteria from adhering to a submerged surface in a particular system will vary somewhat depending on the aqueous system to be protected, the conditions for microbial growth, the extent of any existing biofouling, and the degree of biofouling control desired. For a particular application, the amount of choice may be determined by routine testing of various amounts prior to treatment of the entire affected system. In general, an effective amount used in an aqueous system may range from about 1 to about 500 parts per million and more preferably from about 20 to about 100 parts per million of the aqueous system.

The fluorosurfactant is an anionic or nonionic fluorsurfactant selected from $R_2CH_2CH_2SCH_2CH_2CO_2Li$, $(R_fCH_2CH_2O) P (O) (ONH_4)_2$, $(R_fCH_2CH_2O)_2P(O)(ONH_4)$, $(R_fCH_2CH_2O)P(O) (OH)_2$, $(R_fCH_2CH_2O)_2P(O)(OH)$, $R_fCH_2CH_2O (CH_2CH_2O)_xH$, $R_fCH_2CH_2O(CH_2CH_2O)_yH$, $R_fCH_2CH_2SO_3H$, or mixtures thereof. In these fluorosurfactants, $R_f$ is $F(CF_2CF_2)_{3-8}$, x and y each vary independently from 2 to 20 and more preferably from 5 to 12. The fluorosurfactants useful in the present invention are available from DuPont Chemical Company and are sold as ZONYL® fluorosurfactants.

The methods according to the invention may be part of an overall water treatment regimen. The fluorosurfactant may be used with other water treatment chemicals, particularly with biocides (e.g., algicides, fungicides, bactericides, molluscicides, oxidizers, etc.), stain removers, clarifiers, flocculants, coagulants, or other chemicals commonly used in water treatment. For example, submergible surfaces may be contacted with a fluorosurfactant as a pretreatment to inhibit bacterial adhesion and placed in aqueous system using a microbicide to control the growth of microorganisms. Or, an aqueous system experiencing heavy biological fouling may first be treated with an appropriate biocide to overcome the existing fouling. A fluorosurfactant may then be employed to maintain the aqueous system. Alternatively, a fluorosurfactant may be used in combination with a biocide to inhibit bacteria from adhering to submerged surfaces within the aqueous system while the biocide acts to control the growth of microorganisms in the aqueous system. Such a combination generally allows less microbicide to be used.

"Controlling the growth of the microorganisms" in an aqueous system means control to, at, or below a desired level and for a desired period of time for the particular system. This can be eliminating the microorganisms or preventing their growth in the aqueous systems.

The fluorosurfactant may be used in the methods of the invention as a solid or liquid formulation. Accordingly, the present invention also relates to a composition containing a fluorosurfactant. The composition comprises at least one fluorosurfactant in an amount effective to inhibit bacteria from adhering to a submergible surface or a submerged surface within an aqueous system. When used in combination with another water treatment chemical such as a biocide, the composition may also contain that chemical. If formulated together, the fluorosurfactant and water treatment chemical should not undergo adverse interactions that would reduce or eliminate their efficacy in the aqueous system. Separate formulations are preferred where adverse interactions may occur.

Depending on its use, a composition according to the present invention may be prepared in various forms known in the art. For example, the composition may be prepared in liquid form as a solution, dispersion, emulsion, suspension, or paste; a dispersion, suspension, or paste in a non-solvent; or as a solution by dissolving the fluorosurfactant in a solvent or combination of solvents. Suitable solvents include, but are not limited to, acetone, glycols, alcohols (such as isopropanol), ethers, or other water-dispersible solvents.

Aqueous formulations are preferred. The composition may be prepared as a liquid concentrate for dilution prior to its intended use. Common additives such as surfactants, emulsifiers, dispersants, and the like may be used as known in the art to increase the solubility of the fluorosurfactant or other components in a liquid composition or system, such as an aqueous composition or system. In many cases, the composition of the invention may be solubilized by simple agitation. Dyes or fragrances may also be added for appropriate applications such as toilet waters.

A composition of the present invention may also be prepared in solid form. For example, the fluorosurfactant may be formulated as a powder or tablet using means known in the art. The tablets may contain a variety of excipient known in the tableting art such as dyes or other coloring agents, and perfumes or fragrances. Other components known in the art such as fillers, binders, glidants, lubricants, or antiadherents may also be included. These latter components may be included to improve tablet properties and/or the tableting process.

The following illustrative examples are given to disclose the nature of the invention more clearly. It is to be understood, however, that the invention is not limited to the specific conditions or details set forth in those examples.

EXAMPLES

Test Method: The following method effectively defines the ability of a chemical compound to inhibit bacterial adhesion, or attack the formation of existing attached bacteria on various types of surfaces. As an overview, bioreactors were constructed in which approximately 1 in.×3 in. slides (glass or polystyrene) were fixed to the edge of the bioreactor. The lower ends (approx. 2 in.) of the slides dipped into a bacterial growth medium pH 7 within the bioreactor which contained a known concentration of the test chemical. Following inoculation with known bacterial species, the test solutions were stirred continuously for 3 days. Unless otherwise indicated in the results below, the medium within the bioreactor was turbid by the end of three days. This turbidity indicated that the bacteria proliferated in the medium despite the presence of the chemical tested. This also shows that the chemical, at the concentration tested, showed substantially no biocide (bactericidal) activity. A staining procedure was then used on the slides in order to determine the amount of bacteria attached to the surfaces of the slides.

Construction of Bioreactors: The bioreactors comprised a 400 ml glass beaker over which a lid (cover from a standard 9 cm diameter glass petri dish) was placed. With the lid removed, slides of the material of choice were taped at one end with masking tape and suspended inside the bioreactor from the top edge of the beaker. This allows the slides to be submerged within the test medium. Typically, four slides (replicates) were uniformly spaced around the bioreactor. The score presented below are the average of the four replicates. A magnetic stirring bar was placed in the bottom of the unit, the lid positioned, and the bioreactor autoclaved. Glass slides were used as examples of hydrophillic surfaces and polystyrene (polystyr.) as examples of hydrophobic surfaces. Bacterial Growth Medium: The liquid medium utilized in the bioreactors was described previously by Delaquis, et al., "Detachment Of *Pseudomonas fluorescens* From Biofilms On Glass Surfaces In Response To Nutrient Stress", Microbial Ecology 18:199–210, 1989. The composition of the medium was:

| Glucose | 1.0 g |
|---|---|
| $K_2HPO_4$ | 5.2 g |
| $KH_2PO_4$ | 2.7 g |
| NaCl | 2.0 g |
| $NH_4Cl$ | 1.0 g |
| $MgSO_4.7H_2O$ | 0.12 g |
| Trace Element | 1.0 ml |
| Deionized $H_2O$ | 1.0 L |
| Trace Element Solution: | |
| $CaCl_2$ | 1.5 g |
| $FeSO_4.7H_2O$ | 1.0 g |
| $MnSO_4.2H_2O$ | 0.35 g |
| $NaMoO_4$ | 0.5 g |
| Deionized $H_2O$ | 1.0 L |

The medium was autoclaved and then allowed to cool. If a sediment formed in the autoclaved medium, the medium was resuspended by shaking before use.

Preparation of Bacterial Inocula: Bacteria of the genera *Bacillus, Flavobacterium,* and *Pseudomonas* were isolated from a paper mill slime deposit and maintained in continuous culture. The test organisms were separately streaked onto plate count agar and incubated at 30° C. for 24 hours. With a sterile cotton swab, portions of the colonies were removed and suspended in sterile water. The suspensions were mixed very well and were adjusted to an optical density of 0.858 (*Bacillus*), 0.625 (*Flavobacterium*), and 0.775 (*Pseudomonas*) at 686 nm.

Biofilm Production/Chemical Testing: To four separate bioreactors was added 200 ml of the sterile medium prepared above. Chemicals to be evaluated were first prepared as a stock solution (40 mg/2 ml) using either water or a 9:1 acetone: methanol mixture (acet./MeOH) as a solvent. A 1.0 ml aliquot of the stock solution was added to the bioreactor using moderate, continuous magnetic stirring. This provided an initial concentration of 100 ppm for the test compound. One bioreactor (Control) contains no test compound. Aliquots (0.5 ml) from each of the three bacterial suspensions were then introduced into each bioreactor. The bioreactors were then provided with continuous stirring for three days to allow for proliferation of the bacterial population and deposition of cells onto the surfaces of the slides.

Evaluation of Results: ZONYL® FSA fluorosurfactant and ZONYL® FSN fluorosurfactant were evaluated using the above procedure. After the test was complete, the slides were removed from the bioreactors and were positioned vertically to permit air drying. The degree of adhesion of bacteria to the test surface was then estimated using a staining procedure. The slides were briefly flamed in order to fix the cells to the surface, and then transferred for two minutes to a container of Gram Crystal Violet (DIFCO Laboratories, Detroit, Mich.). The slides were gently rinsed under running tap water, and then carefully blotted. The degree of bacterial adhesion was then determined by visual examination and subjective scoring of each slide. The intensity of the stain is directly proportional to the amount of bacterial adhesion.

The following biofilm scores are given:

| 0 = essentially none | 3 = moderate |
|---|---|
| 1 = scant | 4 = heavy |
| 2 = slight | |

Chemical treatments were evaluated relative to the Control which typically receive an average score for the four bioreactor slides in the 3–4 range. Compounds which receive an average score in the 0–2 range were considered effective to prevent the adhesion of bacteria to the submerged slides. The results are shown in the following Table.

| Compound | Solvent | Conc. ppm | MIC[1] | Slides | Score |
|---|---|---|---|---|---|
| ZONYL ® FSA | acetone | 100 | >500 | glass | 1 |
| ZONYL ® FSA | acetone | 100 | | polystyr. | 0 |

-continued

| Compound | Solvent | Conc. ppm | MIC[1] | Slides | Score |
|---|---|---|---|---|---|
| ZONYL® FSN | acetone | 100 | >500 | glass | 1 |
| ZONYL® FSN | acetone | 100 | | polystyr. | 0 |

[1]Minimum Inhibitory Concentration (MIC) for each compound against the bacteria *E. Aerogenes* using an 18 hour Basal Salts test both at pH 6 and at pH 8 unless otherwise noted.
ZONYL® FSA fluorosurfactant is a product of DuPont Chemicals, Wilmington Delaware. ZONYL® FSA fluorosurfactant contains 23–25 wt % lithium 3-[(1H,1H,2H,2H-flouroalkyl)thiopropionate (CAS No. 65530-69-0); 0–2 wt % telomer B 2-carboxyethyl sulfide (CAS No. 65530-83-8); 35–40 wt % isopropyl alcohol (CAS No. 67-63-0); and 35–40 wt % water. ZONYL® FSN fluorosurfactant is a product available from DuPont Chemicals, Wilmington, Delaware. The ZONYL® FSN product contains 40 wt % $R_fCH_2CH_2O(CH_2CH_2O)_{12}H$, where $R_f$ is $F(CF_2CF_2)_{3-8}$, (CAS No. 65545-80-4); 30 wt % isopropyl alcohol (CAS No. 67-63-0); 30 wt % water; and less than 0.1 wt % 1,4-dioxane (CAS No. 123-91-1).

Minimum Inhibitory Concentration (MIC) for each compound against the bacteria *E. Aerogenes* using an 18 hour Basal Salts test both at pH 6 and at pH 8 unless otherwise noted.

ZONYL® FSA fluorosurfactant is a product of DuPont Chemicals, Wilmington, Del. ZONYL® FSA fluorosurfactant contains 23–25 wt 5 lithium 3-[(1H,1H,2H,2H-flouroalkyl)thiopropionate (CAS No. 65530-69-0); 2–2 wt. % telomer B 2-carboxyethyl sulfide (CAS No. 65530-83-8); 35-40 wt % isopropyl alcohol (CAS No. 67-63-0); and 35–40 wt % water. ZONYL® FSN fluorosurfactant is a product available m DuPont Chemicals, Wilmington, Del. The ZONYL® FSN duct contains 40 wt % $R_fCH_2CH_2O(CH_2CH_2O)_{12}H$, where $R_f$ is $F(CF_2CF_2)_{3-8}$, (CAS No. 65545-80-4); 30 wt % isopropyl alcohol (CAS No. 67-63-0); 30 wt % water; and less than 0.1 wt % 1,4-dioxane (CAS No. 123-91-1).

While particular embodiments of the invention have been described, it will be understood, of course, that the invention is limited to those embodiments. Other modifications may be made. The appended claims are intended to cover any such modifications as fall within the true spirit and scope of the invention.

The claimed invention is:

1. A method to inhibit bacteria from adhering to a submergible surface comprising the step of contacting the submergible surface with at least one anionic or nonionic fluorosurfactant in an amount effective to inhibit bacteria from adhering to the submergible surface without substantially killing the bacteria, wherein the fluorosurfactant is selected from the group consisting of: $R_fCH_2CH_2SCH_2CH_2CO_2Li$, $(R_fCH_2CH_2O)P(O)(ONH_4)_2$, $(R_fCH_2CH_2O)_2P(O)(ONH_4)$, $(R_fCH_2CH_2O)P(O)(OH)_2$, $R_fCH_2CH_2O)_2P(O)(OH)$, $R_fCH_2CH_2O(CH_2CH_2O)_xH$, $R_fCH_2CH_2O(CH_2CH_2O)_yH$, $R_fCH_2CH_2SO_3H$, or mixtures thereof, wherein $R_f$ is $F(CF_2CF_2)_{3-8}$, x varies from 2–20, and y varies from 2–20, and wherein the submergible surface is a ship hull, a boat hull, a marine structure, or a surface of an aqueous system.

2. A method of claim 1, wherein x varies from 5–12 and y varies from 5–12.

3. A method of claim 1, wherein the fluorosurfactant is $R_fCH_2CH_2SCH_2CH_2CO_2Li$, or $R_fCH_2CH_2O(CH_2CH_2O)_{12}H$, wherein $R_f$ is $F(CF_2CF_2)_{3-8}$.

4. A method for controlling biofouling of an aqueous system comprising the step of adding to the aqueous system at least one anionic or nonionic fluorosurfactant in an amount effective to inhibit bacteria from adhering to a submerged surface within the aqueous system without substantially killing the bacteria, wherein the fluorosurfactant is selected from the group consisting of: $R_fCH_2CH_2SCH_2CH_2CO_2Li$, $(R_fCH_2CH_2O)P(O)(ONH_4)_2$, $(R_fCH_2CH_2O)_2P(O)(ONH_4)$, $(R_fCH_2CH_2O)P(O)(OH)_2$, $(R_fCH_2CH_2O)_2P(O)(OH)$, $R_fCH_2CH_2O(CH_2CH_2O)_xH$, $R_fCH_2CH_2O(CH_2CH_2O)_yH$, $R_fCH_2CH_2SO_3H$, or mixtures thereof, wherein $R_f$ is $F(CF_2CF_2)_{3-8}$, x varies from 2–20, and y varies from 2–20, and wherein the submerged surface is a ship hull, a boat hull, a marine structure, or a surface of an aqueous system.

5. A method of claim 4, wherein x varies from 5–12 and y varies from 5–12.

6. A method of claim 4, wherein the fluorosurfactant is $R_fCH_2CH_2SCH_2CH_2CO_2Li$, or $R_fCH_2CH_2O(CH_2CH_2)_{12}H$, wherein $R_f$ is $F(CF_2CF_2)_{3-8}$.

7. A method of claim 6, wherein the fluorosurfactant further reduces any existing biofouling in the aqueous system.

8. A method of claim 4, wherein the effective amount of the fluorosurfactant ranges from 10 ppm to 500 ppm.

9. A method of claim 4, wherein the fluorosurfactant further reduces any existing biofouling in the aqueous system.

10. A method of claim 9, wherein the recreational water system is selected from the group consisting of a swimming pool, a fountain, an ornamental pond, an ornamental pool, and an ornamental stream.

11. A method of claim 4, wherein the aqueous system is an industrial water system.

12. A method of claim 11, wherein the industrial water system is selected from the group consisting of a cooling water system, a metal working fluid system, a papermaking water system, and a textile manufacture water system.

13. A method of claim 4, wherein the aqueous system is a recreational water system.

14. A method of claim 4, wherein the aqueous system is a sanitation water system.

15. A method of claim 14, wherein the sanitation water system is selected from the group consisting of a toilet water- system, a water treatment system, and a sewage treatment system.

16. A method of claim 4, further comprising the step of adding an effective amount of a biocide to the aqueous system to control the growth of a microorganism in the aqueous system.

17. A method of claim 16, wherein the biocide is added prior to the fluorosurfactant to substantially reduce any existing biofouling in the aqueous system and the fluorosurfactant is added to prevent the adhesion of surviving microorganisms to a submerged surfaces within the aqueous system.

18. A method of claim 16, wherein the microorganism is selected from the group consisting of algae, fungi, and bacteria.

19. A method of claim 18, wherein said aqueous system is selected from the group consisting of an industrial water system, a recreational water system, and a sanitation water system.

20. A method of claim 16, wherein a biocide is added concurrently with the fluorosurfactant.

21. A composition for controlling biofouling of an aqueous system, comprising at least one anionic or nonionic fluorosurfactant in an amount effective to inhibit bacteria from adhering to a submerged surface within the aqueous system without substantially killing the bacteria, wherein the fluorosurfactant is selected from the group consisting of: $R_fCH_2CH_2SCH_2CH_2CO_2Li$, $(R_fCH_2CH_2O)P(O)(ONH_4)_2$, $(R_fCH_2CH_2O)_2P(O)(ONH_4)$, $(R_fCH_2CH_2O)P(O)(OH)_2$, $(R_fCH_2CH_2O)_2P(O)(OH)$, $R_fCH_2CH_2O(CH_2CH_2O)_xH$, $R_fCH_2CH_2O(CH_2CH_2O)_yH$, $R_fCH_2CH_2SO_3H$, or mixtures thereof, wherein $R_f$ is $F(CF_2CF_2)_{3-8}$, x varies from 2–20, and y varies from 2–20, and wherein the submerged surface is a ship hull, a boat hull, a marine structure, or a surface of an aqueous system.

22. A composition of claim 21, wherein x varies from 5–12 and y varies from 5–12.

23. A composition of claim 21, wherein the fluorosurfactant is $R_fCH_2CH_2SCH_2CH_2CO_2Li$, or $R_fCH_2CH_2O(CH_2CH_2O)_{12}H$, wherein $R_f$ is $F(CF_2CF_2)_{3-8}$.

24. A composition of claim 21, further comprising a biocide in an amount effective to control the growth of a microorganism in the aqueous system.

25. A composition of claim 21, wherein the composition is in liquid form.

26. A composition of claim 21, wherein the composition is in solid form.

* * * * *